(12) United States Patent
Ketley et al.

(10) Patent No.: US 6,822,007 B2
(45) Date of Patent: Nov. 23, 2004

(54) PROCESS FOR CONVERTING SYNTHESIS GAS INTO HIGHER HYDROCARBONS

(75) Inventors: Graham Walter Ketley, Naperville, IL (US); Barry Nay, Woking (GB); David Newton, Farnham (GB)

(73) Assignee: BP Exploration Operating Company Limited, London (GB)

( * ) Notice: Subject to any disclaimer, the term of this patent is extended or adjusted under 35 U.S.C. 154(b) by 0 days.

(21) Appl. No.: 10/739,284

(22) Filed: Dec. 19, 2003

(65) Prior Publication Data

US 2004/0132839 A1 Jul. 8, 2004

Related U.S. Application Data

(62) Division of application No. 10/463,445, filed on Jun. 18, 2003, now Pat. No. 6,689,330, which is a division of application No. 10/155,359, filed on May 28, 2002, now Pat. No. 6,635,682, which is a continuation of application No. PCT/GB00/04444, filed on Nov. 22, 2000.

(30) Foreign Application Priority Data

Nov. 26, 1999 (GB) .............................. 9928132

(51) Int. Cl.[7] .............................. C07C 27/00
(52) U.S. Cl. ................ 518/712; 518/700; 518/705; 518/715
(58) Field of Search .............. 518/712, 700, 518/705, 715

(56) References Cited

U.S. PATENT DOCUMENTS 5,621,155 A    4/1997  Benham et al. ............. 518/310
6,635,682 B2 * 10/2003  Ketley et al. ............... 518/712

FOREIGN PATENT DOCUMENTS

GB                728543            4/1955

* cited by examiner

Primary Examiner—J. Parsa
(74) Attorney, Agent, or Firm—Nixon & Vanderhye

(57) ABSTRACT

Apparatus suitable for the conversion of synthesis gas to liquid hydrocarbon products, comprising a plurality of injector-mixing nozzles, a tank reactor, a gas recycle line having a first end and a second end and a slurry recycle line having a first end and a second end. The plurality of injector-mixing nozzles is arranged at or near the top of the tank reactor, each injector mixing nozzle having a first inlet for a suspension of a catalyst in a liquid medium, at least one second inlet for synthesis gas and an outlet positioned within the tank reactor for discharging a mixture of synthesis gas and the suspension from the injector-mixing nozzles in a downwards direction into the tank reactor. The tank reactor has a first outlet for discharging a product suspension at or near the bottom thereof and a second outlet for a gaseous recycle stream at or near the top thereof. The first end of the slurry recycle line is in communication with the first outlet of the tank reactor and the second end of the slurry recycle loop is in communication with the first inlet of the injector-mixing nozzles. The first end of the gas recycle line is in communication with the second outlet of the tank reactor and the second end of the gas recycle line is in communication with the second inlet(s) of the injector-mixing nozzles.

35 Claims, 1 Drawing Sheet

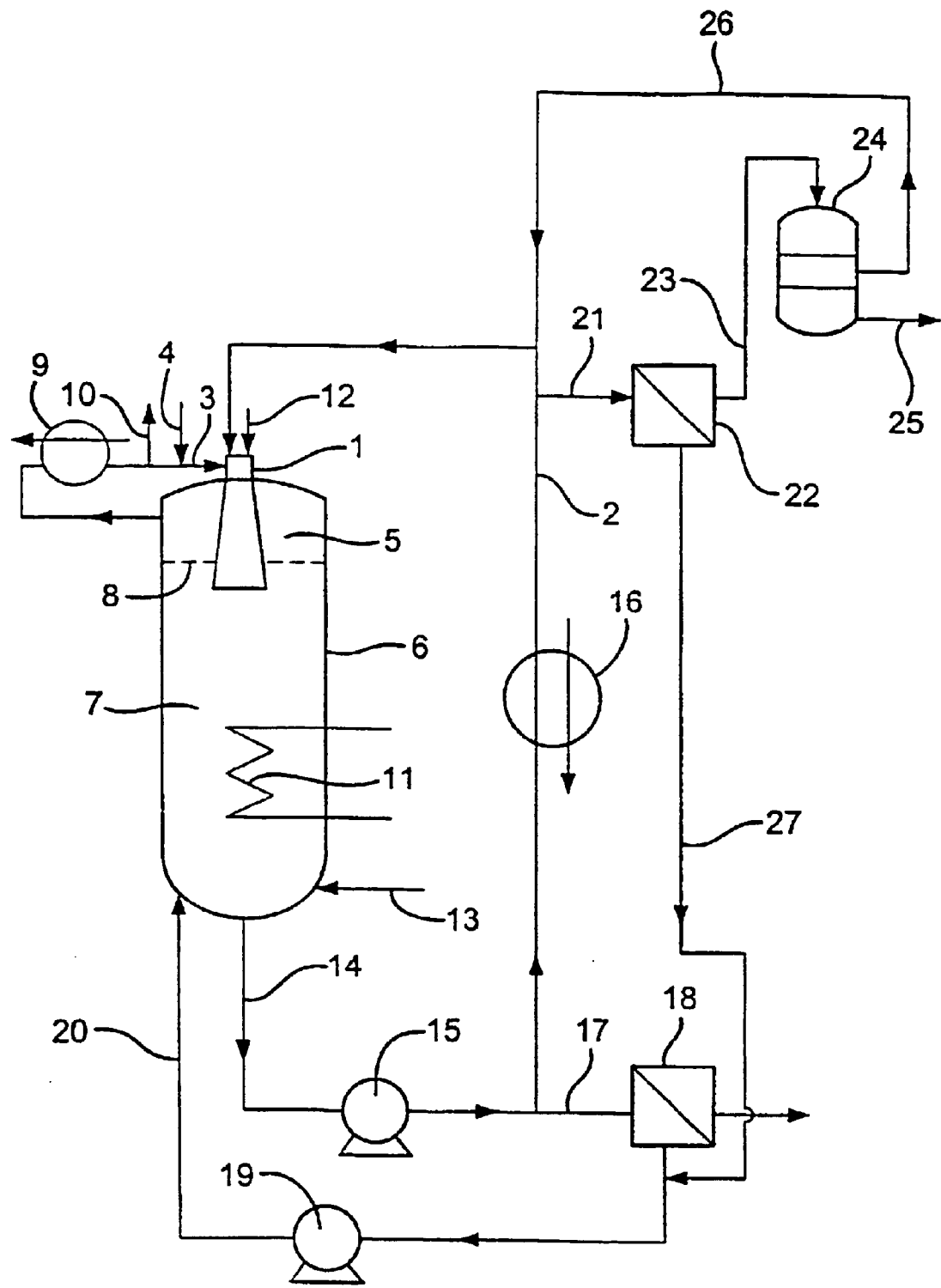

PROCESS FOR CONVERTING SYNTHESIS GAS INTO HIGHER HYDROCARBONS

This application is a Divisional of application Ser. No. 10/463,445, filed Jun. 18, 2003, now U.S. Pat. No. 6,689,330, granted Feb. 10, 2004, which is a Divisional of application Ser. No. 10/155,359, filed May 28, 2002, now U.S. Pat. No. 6,635,682, granted Oct. 21, 2003, the entire content of which is hereby incorporated by reference in this application, which is a continuation of PCT/GB00/04444 filed Nov. 22, 2003.

BACKGROUND OF THE INVENTION

The present invention relates to a process for the conversion of carbon monoxide and hydrogen (synthesis gas) to liquid hydrocarbon products in the presence of a Fischer-Tropsch catalyst.

In the Fischer-Tropsch reaction a gaseous mixture of carbon monoxide and hydrogen is reacted in the presence of a heterogeneous catalyst to give a hydrocarbon mixture having a relatively broad molecular weight distribution. This product is predominantly straight chain, saturated hydrocarbons which typically have a chain length of more than 5 carbon atoms. The reaction is highly exothermic and therefore heat removal is one of the primary constraints of all Fischer-Tropsch processes. This has directed commercial processes away from fixed bed operation to slurry systems. Such slurry systems employ a suspension of catalyst particles in a liquid medium thereby allowing both the gross temperature control and the local temperature control (in the vicinity of individual catalyst particles) to be significantly improved compared with fixed bed operation.

Fischer-Tropsch processes are known which employ slurry bubble columns in which the catalyst is primarily distributed and suspended in the slurry by the energy imparted from the synthesis gas rising from the gas distribution means at the bottom of the slurry bubble column as described in, for example, U.S. Pat. No. 5,252,613.

The Fischer-Tropsch process may also be operated by passing a stream of the liquid medium through a catalyst bed to support and disperse the catalyst, as described in U.S. Pat. No. 5,776,988. In this approach the catalyst is more uniformly dispersed throughout the liquid medium allowing improvements in the operability and productivity of the process to be obtained.

However, there remains the need for further improvements in the mode of operation of a Fischer-Tropsch process.

SUMMARY OF THE INVENTION

The present invention relates to a process for the conversion of gaseous reactants to liquid hydrocarbon products by contacting the gaseous reactants at an elevated temperature and pressure with a suspension comprising catalyst suspended in a liquid medium, in a system comprising a high shear mixing zone and a post mixing zone wherein the process comprises:

a) passing the suspension comprising catalyst suspended in the liquid medium through the high shear mixing zone where a gaseous reactant stream comprising the gaseous reactants is mixed with the suspension;

b) discharging a mixture comprising gaseous reactants and suspension from the high shear mixing zone into the post mixing zone;

c) converting at least a portion of the gaseous reactants to liquid hydrocarbon products in the post mixing zone to form a product suspension comprising catalyst suspended in the liquid medium and the liquid hydrocarbon products;

d) separating a gaseous stream comprising unconverted gaseous reactants from the product suspension;

e) recycling the separated gaseous stream to the high shear mixing zone; and f) recycling at least a portion of the product suspension to the high shear mixing zone.

An advantage of the process of the present invention over conventional Fischer-Trospch processes is that enhanced mass transfer in the high shear mixing zone and the post mixing zone improves the contact between the gaseous reactants, liquid medium and solid catalyst and hence promotes the catalytic conversion of the gaseous reactants to liquid hydrocarbon products. For avoidance of doubt, the conversion of the gaseous reactants to liquid hydrocarbon products is initiated in the high shear mixing zone although the majority of the conversion generally occurs in the post mixing zone.

Preferably, the gaseous reactants comprise a mixture of carbon monoxide and hydrogen (synthesis gas). Preferably, the ratio of hydrogen to carbon monoxide in the synthesis gas is 2:1 by volume.

The synthesis gas may be prepared using any of the processes known in the art including partial oxidation of hydrocarbons, steam reforming, and autothermal reforming. A discussion of these synthesis gas production technologies is provided in "Hydrocarbon Processing" V78, N.4, 87–90, 92–93 (April 1999) and "Petrole et Techniques", N. 415, 86–93 (July–August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187–196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 6769; "Hydrocarbon Processing", 79/9, 34 (September 2000); "Today's Refinery", 15/8, 9 (August 2000); WO 99/02254; and WO 200023689.

Preferably, the liquid hydrocarbon products comprise a mixture of hydrocarbons having a chain length of greater than 5 carbon atoms. Suitably, the liquid hydrocarbon products comprise a mixture of hydrocarbons having chain lengths of from 5 to about 90 carbon atoms. Preferably, a major amount, for example, greater than 60% by weight, of the hydrocarbons have chain lengths of from 5 to 30 carbon atoms.

Suitably, the liquid medium comprises one or more of the liquid hydrocarbon products which has the advantage that there is no requirement to separate the liquid hydrocarbon products from the liquid medium.

The high shear mixing zone may be part of the system inside or partially outside the post mixing zone, for example, the high shear mixing zone may project through the walls of the post mixing zone such that the high shear mixing zone discharges its contents into the post mixing zone. The system may comprise a plurality of high shear mixing zones, preferably up to 250 high shear mixing zones, more preferably less than 100, most preferably less than 50, for example 10 to 50 high shear mixing zones. Preferably, the plurality of high shear mixing zones discharge into a single post mixing zone which has an advantage of significantly reducing the size of a commercial Fischer-Tropsch plant. Preferably, the plurality of high shear mixing zones may be spaced uniformly inside or partially outside the post mixing zone, for example, the high shear mixing zones may be spaced uniformly at or near the top of the post mixing zone. Preferably, the high shear mixing zones discharge the mixture of gaseous reactants and suspension in a downwards direction into the post mixing zone.

The high shear mixing zone(s) may comprise any device suitable for intensive mixing or dispersing of a gaseous stream in a suspension of solids in a liquid medium, for example, a rotor-stator device or an injector-mixing nozzle.

The injector-mixing nozzle(s) can advantageously be executed as venturi tubes (c.f. "Chemical Engineers' Handbook" by J. H. Perry, $3^{rd}$ edition (1953), p. 1285, FIG. 6I), preferably an injector mixer (c.f. "Chemical Engineers' Handbook" by J H Perry, $3^{rd}$ edition (1953), p 1203, FIG. 2 and "Chemical Engineers' Handbook" by R H Perry and C H Chilton $5^{th}$ edition (1973) p 6–15, FIGS. 6–31) or most preferably as a liquid-jet ejector (c.f. "Unit Operations" by G G Brown et al, $4^{th}$ edition (1953), p. 194, FIG. 210). Alternatively, the injector-mixing nozzle(s) may be executed as "gas blast" or "gas assist" nozzles where gas expansion is used to drive the nozzle (c.f. "Atomisation and Sprays" by Arthur H Lefebvre, Hemisphere Publishing Corporation, 1989). Where the injector-mixing nozzle(s) is executed as a "gas blast" or "gas assist" nozzle, the suspension of catalyst is fed to the nozzle at a sufficiently high pressure to allow the suspension to pass through the nozzle while the gaseous reactant stream is fed to the nozzle at a sufficiently high pressure to achieve high shear mixing within the nozzle.

Suitably, the gaseous reactant stream is fed to the high shear mixing zone at a pressure of at least 20 bar, preferably at least 30 bar. Typically, the pressure drop of the suspension over the high shear mixing zone is in the range of from 1 to 6 bar, preferably 2 to 5 bar, more preferably 3 to 4 bar. An advantage of the process of the present invention is that where the gaseous reactant stream comprises synthesis gas obtained via a "Compact Reformer" process, the synthesis gas is generally at a pressure of above 20 bar. Accordingly, there is no requirement to lower the pressure of the synthesis gas before feeding the synthesis gas to the process of the present invention thereby providing an energy efficient integrated Reforming/Fischer Tropsch process. In particular, the pressure of synthesis gas obtained via a "Compact Reformer" process is generally sufficiently high to achieve high shear mixing within a "gas blast" or "gas assist" nozzle.

Suitably, the shear forces exerted on the suspension in the high shear mixing zone(s) are sufficiently high that the gaseous reactant stream is broken down into gas bubbles having diameters in the range of from $30\mu$ to 10 mm, preferably from $30\mu$ to $3000\mu$, more preferably from $30\mu$ to $300\mu$.

Preferably, the product suspension which is recycled to the high shear mixing zone (hereinafter referred to as "suspension recycle stream") is cooled outside of the high shear mixing zone and the post mixing zone, in order to assist in the removal of exothermic heat of reaction from the system, for example, by passing the suspension recycle stream through a heat exchanger. Preferably, the suspension recycle stream is cooled to a temperature of not more than 12° C. below the temperature of the suspension in the post mixing zone.

Preferably, additional cooling is provided within the post mixing zone by means of a heat exchanger, for example, heat transfer tubes, positioned within the suspension in the post mixing zone.

The gaseous stream comprising unconverted gaseous reactants may be separated from the product suspension either within the post mixing zone or in an external gas liquid separation zone. The separated gaseous stream may comprise vaporized low boiling liquid hydrocarbon products, vaporized water by-product and gaseous hydrocarbons having from 1 to 3 carbon atoms such as methane, ethane and propane, in addition to unconverted gaseous reactants.

The separated gaseous stream (hereinafter referred to as "gaseous recycle stream") may be cooled before being recycled to the high shear mixing zone, for example, by passing the gaseous recycle stream through a heat exchanger, to assist in the removal of the exothermic heat of reaction from the system. Where the gaseous recycle stream is cooled to below its dew point, any vaporized low boiling liquid hydrocarbon products and any vaporized water by-product will condense out of the gaseous recycle stream and these condensed liquids are preferably removed from the system using a suitable separation means, for example, the heat exchanger may be fitted with a liquid trap. Water by-product may then be separated from the condensed low boiling liquid hydrocarbon products using a suitable separation means, such as a decanter. The low boiling hydrocarbon products may then be recycled to the high shear mixing zone and/or the post mixing zone. Fresh gaseous reactants may be fed to the gaseous recycle stream, either upstream or downstream of the heat exchanger. Where the fresh gaseous reactants have not been pre-cooled, it is preferred that the fresh gaseous reactants are fed to the gaseous recycle stream upstream of the heat exchanger. Preferably, the gaseous stream which is recycled to the high shear mixing zone comprises from 5 to 50% by volume of fresh gaseous reactants.

Preferably, a purge stream is taken from the gaseous recycle stream to prevent accumulation of gaseous by-products, for example, methane, in the system. If desired, any gaseous intermediate products (gaseous hydrocarbons having 2 or 3 carbon atoms) may be separated from the purge stream. Preferably, such gaseous intermediate products are recycled to the system where they may be converted to liquid hydrocarbon products.

Preferably, a stream comprising low boiling hydrocarbon (s) (for example pentanes, hexanes or hexenes) may be introduced into the high shear mixing zone and/or the post mixing zone. Without wishing to be bound by any theory, it is believed that vaporisation of the low boiling hydrocarbon (s) (hereinafter referred to as "low boiling solvent") in the high shear mixing zone and/or the post mixing zone aids and enhances the mixing of the gaseous reactants, liquid medium and the solid catalyst thereby increasing conversion of the gaseous reactants to liquid hydrocarbon products. Moreover, vaporisation of the low boiling solvent will also assist in removing some of the exothermic heat of reaction thereby allowing more control over the product selectivities and minimising the production of gaseous by-products, for example, methane. For avoidance of doubt, it is envisaged that the low boiling solvent may vaporise in both the post mixing zone and the high shear mixing zone. The gaseous recycle stream may therefore comprise vaporized low boiling solvent in addition to vaporized low boiling liquid hydrocarbon products, vaporized water by-product, unconverted gaseous reactants and gaseous hydrocarbons having from 1 to 3 carbon atoms. As discussed above, the gaseous recycle stream may be cooled before being recycled to the high shear mixing zone. Any vaporized low boiling solvent may condense, together with any vaporized low boiling liquid hydrocarbon products and any vaporized water by-product, upon cooling the gaseous recycle stream to below its dew point. Preferably, the condensed liquids are removed from the system, as described above, and water by-product may then be separated from the condensed liquids using a suitable separation means, also as described above. The remaining condensed liquids may then be recycled to the high shear mixing zone and/or the post mixing zone.

For practical reasons the post mixing zone may not be totally filled with suspension during the process of the present invention so that above a certain level of suspension a gas cap containing unconverted gaseous reactants is present in the top of post mixing zone. Suitably, the volume of the gas cap is not more than 40%, preferably not more than 30% of the volume of the post mixing zone. The high shear mixing zone may discharge into the post mixing zone either above or below the level of suspension in the post mixing zone. An advantage of the high shear mixing zone discharging below the level of suspension is that this improves the contact between the gaseous reactants and the suspension in the post mixing zone.

Where the post mixing zone has a gas cap, the gaseous recycle stream may be withdrawn from the gas cap. It is also envisaged that the post mixing zone may be fitted with an overhead condenser or cooler for removal of heat from the gases in the gas cap. Where the post mixing zone is fitted with an overhead condenser or cooler, the gaseous recycle stream may be withdrawn from the overhead condenser or cooler (i.e. is withdrawn indirectly from the post mixing zone). Any low boiling liquid hydrocarbon products and low boiling solvent which condense in the condenser or cooler may be collected and recycled to the high shear mixing zone or the post mixing zone (after having separated any water by-product).

The catalyst which may be employed in the process of the present invention is any catalyst known to be active in Fischer-Tropsch synthesis. For example, Group VIII metals whether supported or unsupported are known Fischer-Tropsch catalysts. Of these iron, cobalt and ruthenium are preferred, particularly iron and cobalt, most particularly cobalt.

A preferred catalyst is supported on an inorganic refractory oxide. Preferred supports include silica, alumina, silica-alumina, the Group IVB oxides, titania (primarily in the rutile form) and most preferably zinc oxide. The supports generally have a surface area of less than about 100 $m^2/g$, preferably less than 50 $m^2/g$, more preferably less than 25 $m^2/g$, for example, about 5 $m^2/g$.

The catalytic metal is present in catalytically active amounts usually about 1–100 wt %, the upper limit being attained in the case of iron based catalysts, preferably 2–40 wt %. Promoters may be added to the catalyst and are well known in the Fischer-Trospch catalyst art. Promoters can include ruthenium, platinum or palladium (when not the primary catalyst metal), rhenium, hafnium, cerium, lanthanum and zirconium, and are usually present in amounts less than the primary catalytic metal (except for ruthenium which may be present in coequal amounts), but the promoter:metal ratio should be at least 1:10. Preferred promoters are rhenium and hafnium.

A further advantage of the process of the present invention is that intensive mixing of the gaseous reactant stream and the suspension of catalyst in the high shear mixing zone allows smaller catalyst particle sizes to be employed compared with a conventional slurry process. Thus, the catalyst may have a particle size of less than 50 microns, preferably less than 40 microns, for example, in the range 5 to 30 microns. In contrast, a conventional slurry process will typically employ a catalyst having a particle size of greater than 40 microns. Advantages of smaller catalyst particle sizes include reducing the selectivity of the process of the present invention to methane (a gaseous by-product) and also reducing the formation of heavier hydrocarbon products. Without wishing to be bound by any theory, it is believed that catalyst particles having the preferred particle size of less than 40 microns may be formed in situ in the system by attrition of larger sized catalyst particles, for example, by attrition of a catalyst having a particle size of greater than 50 microns.

Preferably, the suspension of catalyst discharged into the post mixing zone comprises less than 40% wt of catalyst particles, more preferably 10 to 30% wt of catalyst particles, most preferably 10 to 20% wt of catalyst particles.

In a preferred embodiment the process is carried out using an injector-mixing nozzle. It has been found that intensive mixing of the gaseous reactant stream, the liquid medium and the solid catalyst can be achieved in the injector-mixing nozzle leading to high conversions of gaseous reactants to liquid hydrocarbon products in the post mixing zone. The suspension which is discharged by the injector-mixing nozzle into the post mixing zone is at least in part recycled to the injector-mixing nozzle, for example, via a slurry pump. The injector-mixing nozzle may draw in the gaseous reactant stream through at least one opening in its side wall (a venturi nozzle). Alternatively, as described above, the gaseous reactant stream may be supplied at high pressure to the injector-mixing nozzle through at least one opening in its side wall (a "gas blast" or "gas assist" nozzle). An advantage of using a "gas blast" or "gas assist" nozzle as the high shear mixing zone is that there is a reduced duty on the slurry pump.

More than one injector-mixing nozzle, preferably up to 150, more preferably less than 100, most preferably less than 50, for example 10 to 50 injector-mixing nozzles may discharge into a single post mixing zone.

Suitably, the post mixing zone comprises a vessel, for example, a tank reactor or a tubular loop conduit and the injector-mixing nozzle can be placed at any position on the walls of the vessel (for example, at the top, bottom or side walls of a tank reactor).

Where the vessel of the post mixing zone is a tank reactor, product suspension is withdrawn from the tank reactor and is at least in part recycled to the injector-mixing nozzle(s). Very good mixing can be achieved when the injector-mixing nozzle(s) is situated at the top of the tank reactor and the suspension is removed from the tank reactor at its bottom. Therefore the tank reactor is preferably provided at its top with at least one injector-mixing nozzle and the suspension recycle stream is preferably withdrawn from the bottom of the tank reactor. Preferably, the suspension recycle stream is at least in part recycled via a loop conduit (slurry recycle line) to the top of the injector-mixing nozzle(s) through which it is then injected into the top of the tank reactor, the gaseous reactant stream being introduced through one or more openings in the side wall of the injector-mixing nozzle(s). Preferably, a heat-exchanger is positioned on the loop conduit to remove the heat of reaction.

Where the vessel of the post mixing zone is a tubular loop conduit, a single injector-mixing nozzle may discharge into the tubular loop conduit. Suspension may be recycled to the injector-mixing nozzle, for example, via a pump or propeller positioned in the tubular loop conduit. A heat exchanger may be disposed along at least part of the length of the tubular loop conduit, preferably along substantially the entire length of the tubular loop conduit thereby providing temperature control. Alternatively, a series of injector-mixing nozzles may be arranged around the tubular loop conduit. In this arrangement each injector-mixing nozzle discharges into a section of the tubular loop conduit which section recycles the suspension to the next injector-mixing nozzle in the loop, for example, via a pump or propeller positioned in the section of the tubular loop conduit. A heat exchanger may be disposed along at least part of each section of tubular loop conduit, preferably along substantially the entire length of each section of tubular loop conduit thereby providing temperature control. It is envisaged that mixing of the gaseous reactants and the suspension of catalyst in the tubular loop conduit may be so efficient that there is no requirement for a gas cap. Where a gas cap is omitted, product suspension together with entrained and/or dissolved gases (unconverted gaseous reactants, gaseous hydrocarbons having from 1 to 3 carbon atoms, vaporized low boiling liquid hydrocarbon products, vaporized water by-product and optionally vaporized low boiling solvent) is withdrawn from the tubular loop conduit and a gaseous recycle stream comprising the entrained and/or dissolved gases is separated from the product suspension in an external gas liquid separation zone.

Where the vessel of the post mixing zone (e.g. tank reactor or tubular loop conduit) has a gas cap, advantageously the gaseous recycle stream is withdrawn through the vessel wall from the gas cap and is recycled to the injector-mixing nozzle(s). As mentioned above, an advantage of recycling the gaseous reactants from the gas cap to the injector-mixing nozzle(s) is that in this manner the temperature of the suspension in the vessel can be advantageously controlled by cooling the gaseous recycle stream in a heat exchanger outside the high shear mixing zone and the vessel of the post mixing zone. This temperature control can be further improved if fresh gaseous reactants are added to the gaseous recycle stream before it is cooled (upstream of the heat exchanger) or are pre-cooled. The temperature of the suspension in a tank reactor can also be controlled by means of a heat exchanger, for example, heat transfer tubes, positioned below the level of suspension in the tank reactor and by means of external cooling of the suspension recycle stream.

The process of the invention is preferably carried out at a temperature of 180–280° C., more preferably 190–240° C.

The process of the invention is preferably carried out at a pressure of 5–50 bar, more preferably 15–35 bar, generally 20–30 bar.

The process of the present invention can be operated in batch or continuous mode, the latter being preferred.

In a continuous process part of the product suspension is continuously removed from the system and is passed to a suitable separation means, where liquid medium and liquid hydrocarbon products are separated from the catalyst. Examples of suitable separation means include hydrocyclones, filters, gravity separators and magnetic separators. Alternatively, the liquid medium and liquid hydrocarbon products may be separated from the catalyst by distillation. The separated liquids are then passed to a product purification stage where water by-product and liquid medium are removed from the liquid hydrocarbon products. As discussed above, the purification stage may be simplified by using one or more of the liquid hydrocarbon products as the liquid medium in which case there is no requirement to separate the liquid medium from the liquid hydrocarbon products. The catalyst may be recycled as a concentrated slurry to the post mixing zone. Fresh catalyst may be added either to the recycled slurry or directly into the post mixing zone.

In order to prevent the accumulation of water by-product in the system it is preferred that at least a portion of the water by-product is removed from the suspension recycle stream. This may be achieved by taking a side stream from the suspension recycle stream downstream of the heat exchanger. The liquid components of the side stream are separated from the catalyst (as described above) and water by-product is removed from the separated liquids (also as described above) before recycling the remaining separated liquid components back to the high shear mixing zone. The separated catalyst may be recycled to the post mixing zone as a concentrated slurry (as described above).

It is envisaged that removal of water by-product from the system can be incorporated into the product separation stage, by recycling a portion of the separated liquids, from which water has been removed, back to the high shear mixing zone.

The liquid hydrocarbon products from the purification stage may be fed to a hydrocracking stage, for example, a catalytic hydrocracking stage which employs a catalyst comprising a metal selected from the group consisting of cobalt, molybdenum, nickel and tungsten supported on a support material such as alumina, silica-alumina or a zeolite. Preferably, the catalyst comprises cobalt/molybdenum or nickel/molybdenum supported on alumina or silica-alumina. Suitable hydrocracking catalysts include catalysts supplied by Akzo Nobel, Criterion, Chevron, or UOP. A preferred catalyst is KF 1022™, a cobalt/molybdenum on alumina catalyst, supplied by Akzo Nobel.

BRIEF DESCRIPTION OF THE DRAWINGS

The invention will now be illustrated with reference to the accompanying FIGURE which is a schematic of the process of the present invention.

DETAILED DESCRIPTION OF PREFERRED EMBODIMENTS

A suspension of a catalyst in a liquid medium is recycled to an injector-mixing nozzle (1) via a line (2). Through one or more openings in the side wall of the injector-mixing nozzle (1) the suspension draws in a gaseous reactant stream comprising carbon monoxide and hydrogen, which is introduced into the injector-mixing nozzle (1) via a line (3). Fresh gaseous reactants are introduced via a line (4) into the line (3) through which unconverted gaseous reactants are recycled from a gas cap (5) which is present in the upper part of a vessel (6) the lower part of which contains a suspension (7) of the catalyst in a mixture of the liquid medium and liquid hydrocarbon products. A dotted line (8) in the Figure denotes the upper level of the suspension (7) in the vessel (6).

By means of cooling in a heat exchanger (9) the gas mixture passing through the line (3) is maintained at the correct operating temperature. Suitably, the heat exchanger (9) is a condenser having a water trap for removing water by-product from the system. A purge stream (10) is taken from the line (3) to prevent the build up of gaseous by-products in the gas cap (5). Optionally, a heat exchanger (11) e.g. cooling tubes is provided below the level of the suspension (7) in the vessel (6) to assist in removing the exothermic heat of reaction.

Optionally, a stream of low boiling hydrocarbon liquid(s) (low boiling solvent) may be introduced to the injector-mixing nozzle (1) via line (12) or alternatively to the vessel (6), via line (13). Where low boiling hydrocarbon liquid(s) are introduced to the system these may condense in the heat exchanger (9). The condensed low boiling hydrocarbon liquid(s) may be separated from the condensed water by-product in a decanter (not shown). The separated low boiling hydrocarbon liquid(s) may then be recycled to the system.

Via a lower outlet opening of the injector-mixing nozzle (1) the mixture of catalyst, liquid medium, liquid hydrocarbon products and unconverted gaseous reactants pass into the vessel (6) below the level (8) of the suspension (7). The unconverted gaseous reactants then separate into the gas cap (5).

Via a line (14) the suspension (7) is withdrawn from the bottom of the vessel (6) and at least a portion of the suspension is recycled to the injector-mixing nozzle (1) by means of pump (15) and the line (2). By means of cooling in a heat exchanger (16) the recycled suspension in the line (2) is maintained at the correct operating temperature.

Via a line (17) a portion of the suspension (7) is withdrawn from the system. By a suitable separation means (18), e.g. a hydrocyclone, filter, gravity separator or magnetic separator, or alternatively, by distillation, the liquid medium and liquid hydrocarbon products may be separated from the suspended catalyst. Separated catalyst may be returned to the vessel (6) as a slurry via a slurry pump (19) and a line (20). The separated liquid medium and liquid hydrocarbon products may be passed from the separation means (18) to a purification zone (not shown).

A portion of suspension may be withdrawn from line (2) and may be passed along line (21) to a separation means (22) where the liquid components of the suspension are separated from the catalyst (e.g., as described above). The separated liquids are then passed along line (23) to a decanter (24) where water by-product is removed from the system via line (25). The remaining liquids are then reintroduced into line (2) via line (26). The separated catalyst, from decanter (24), is introduced as a slurry into line (20) via a line (27).

We claim:

1. A process for the conversion of synthesis gas to liquid hydrocarbon products by contacting the synthesis gas at an elevated temperature and pressure with a suspension comprising catalyst suspended in a liquid medium, in a system comprising a high shear mixing zone and a tubular loop reactor said process comprising the steps of:
   a) passing the suspension comprising catalyst suspended in the liquid medium through the high shear mixing zone where synthesis gas is mixed with the suspension;
   b) discharging a mixture comprising synthesis gas and suspension from the high shear mixing zone into the tubular loop reactor;
   c) converting at least a portion of the synthesis gas to liquid hydrocarbon products in the tubular loop reactor to form a product suspension comprising catalyst suspended in the liquid medium and the liquid hydrocarbon products;
   d) separating a gaseous stream comprising unconverted synthesis gas from the product suspension;
   e) recycling the separated gaseous stream to the high shear mixing zone; and
   f) recycling at least a portion of the product suspension to the high shear mixing zone.

2. A process according to claim 1 wherein the high shear mixing zone is an injector-mixing nozzle.

3. A process according to claim 1 wherein the synthesis gas is broken down in the high shear mixing zone into gas bubbles having diameters in the range $30\mu$ to 10 mm.

4. A process according to claim 3 wherein the synthesis gas is broken down in the high shear mixing zone into gas bubbles having diameters in the range of from $30\mu$ to $3000\mu$.

5. A process according to claim 1 wherein the gaseous recycle stream is cooled before being recycled to the high shear mixing zone.

6. A process according to claim 5 wherein vaporized low boiling liquid hydrocarbon products and vaporized water by-product condense out of the gaseous recycle stream and are removed therefrom.

7. A process according to claim 1 wherein the product suspension is cooled before being recycled to the high shear mixing zone.

8. A process according to claim 7 wherein additional cooling is provided by means of a heat exchanger positioned within the suspension in the tubular loop reactor.

9. A process according to claim 1 wherein the tubular loop reactor contains a gas cap and the high shear mixing zone discharges either above or below the level of suspension in the tubular loop reactor.

10. A process as claimed in claim 9 wherein the gaseous recycle stream is withdrawn from the gas cap and is recycled to the high shear mixing zone.

11. A process according claim 1 wherein the discharge of the mixture comprising synthesis gas and suspension from the high shear mixing zone into the tubular loop reactor is done in a downwards direction.

12. A process according claim 1 wherein product suspension is withdrawn from at or near the bottom of the tank reactor.

13. A process as claimed in claim 1 wherein the suspension is at least in part recycled to the high shear mixing zone via a slurry recycle line and a slurry pump.

14. A process according to claim 13 wherein the slurry recycle line is provided with a heat exchanger.

15. A process according to claim 1 wherein the synthesis gas is fed to the high shear mixing zone at a pressure of at least 20 bar.

16. A process according to claim 1 wherein the pressure drop over the high shear mixing zone is in the range of from 1 to 6 bar.

17. A process according to claim 1 wherein a stream comprising low boiling hydrocarbon(s) is introduced into the high shear mixing zone and/or the tubular loop reactor.

18. A process according to claim 1 wherein the system comprises a plurality of high shear mixing zones which discharge into the tubular reactor.

19. A process as claimed in claim 18 wherein up to 150 injector-mixing nozzles discharge into the tubular reactor.

20. A process according to claim 1 wherein the liquid hydrocarbon products comprise a mixture of hydrocarbons having chain lengths of from 5 to about 90 carbon atoms.

21. A process according to claim 1 wherein the catalyst is iron, cobalt or ruthenium supported on silica, alumina, silica-alumina, titania or zinc oxide.

22. A process according to claim 1 wherein the catalyst has a particle size of less than 50 microns.

23. A process according to claim 1 wherein the catalyst has a particle size in the range 5 to 30 microns.

24. A process according to claim 1 wherein the suspension discharged into the tubular loop reactor comprises 10 to 30% wt of catalyst particles.

25. A process according to claim 1 in which the tubular loop reactor is maintained at a temperature of 180–280° C. and a pressure of 5–50 bar.

26. A process according to claim 1 wherein the high shear mixing zone is a single injector-mixing nozzle which discharges into the tubular loop conduit and wherein suspension is recycled to the injector-mixing nozzle.

27. A process according to claim 1 wherein a heat exchanger is disposed along at least part of the length of the tubular loop conduit.

28. A process according to claim 1 wherein the high shear mixing zone is a series of injector-mixing nozzles which are arranged around the tubular loop conduit.

29. A process according to claim 1 wherein no gas cap is present in the tubular loop.

30. A process according to claim 1 wherein the suspension together with entrained and/or dissolved gases is withdrawn from the tubular loop conduit and a gaseous recycle stream comprising the entrained and/or dissolved gases is separated from the product suspension in an external gas liquid separation zone.

31. A process according to claim 1 wherein the high shear mixing zone is an injector-mixing nozzle executed as a venturi nozzle or a gas blast nozzle.

32. A process according to claim 1 wherein the synthesis gas is fed to the high shear mixing zone at a pressure of at least 30 bar.

33. A process according to claim 1 wherein the high shear mixing zone is a single injector-mixing nozzle which discharges into the tubular loop conduit and wherein suspension is recycled to the injector-mixing nozzle via a pump or propeller positioned in the tubular loop conduit.

34. A process according to claim 1 wherein a heat exchanger is disposed along at least part of the length of the tubular loop conduit along substantially the entire length of the tubular loop conduit.

35. A process according to claim 30 wherein the entrained and/or dissolved gases are unconverted gaseous reactants, gaseous hydrocarbons having from 1 to 3 carbon atoms, vaporized low boiling liquid hydrocarbon products, vaporized water by-product, optionally vaporized low boiling solvent, or mixtures thereof.

* * * * *